United States Patent [19]
Trop

[11] Patent Number: 6,030,213
[45] Date of Patent: Feb. 29, 2000

[54] DEVICE AND METHOD FOR LOCAL APPLICATION OF A MEDICAMENT TO A GINGIVA

[76] Inventor: Ayelet Trop, 65 Hanasi, 38386, Hadera, Israel

[21] Appl. No.: 09/273,267

[22] Filed: Mar. 22, 1999

[51] Int. Cl.[7] .................................................. A61G 17/02
[52] U.S. Cl. ............................................. 433/80; 433/215
[58] Field of Search .................................. 433/80, 6, 37, 433/48, 215, 216, 89, 136; 604/1

[56] References Cited

U.S. PATENT DOCUMENTS

| | | | |
|---|---|---|---|
| 4,064,628 | 12/1977 | Weitzman | 433/80 |
| 4,560,351 | 12/1985 | Osborne | 433/80 |
| 5,085,585 | 2/1992 | Zimble | 433/80 |
| 5,122,056 | 6/1992 | Barbee | 433/80 |
| 5,924,863 | 7/1999 | Jacobs et al. | 433/80 |
| 5,938,438 | 8/1999 | Chipman et al. | 433/80 |

*Primary Examiner*—Gene Mancene
*Assistant Examiner*—Pedro Philogene
*Attorney, Agent, or Firm*—Mark M. Friedman

[57] ABSTRACT

A device and method are provided for local application of a medicament to a gingiva. The device includes (a) at least one absorbent body for absorbing the medicament; and (b) a biasing structure engaging the at least one absorbent body and being sized and so constructed so as to serve as a clip engagable over a tooth or several adjacent teeth of a maxilla or mandibula for biasing the at least one absorbent body against a portion of a maxillary gingiva or a mandibulary gingiva, respectively.

17 Claims, 1 Drawing Sheet

DEVICE AND METHOD FOR LOCAL APPLICATION OF A MEDICAMENT TO A GINGIVA

FIELD AND BACKGROUND OF THE INVENTION

The present invention relates to a device and method for local application of a medicament, such as, but not limited to, a local diffusive anesthetic drug, an antiseptic drug, and/or a therapeutic drug, to a gingiva.

During a dental treatment, it is in many cases desirous to locally apply a medicament. For example, before injecting an anesthetic into the tissue forming the mouth cavity, typically to a gingiva, it is desirous to locally anaesthetize the gingival portion to be injected, so as to prevent the trauma and pain of the injection process itself. This is especially desirous when children are so treated.

To this end, local diffusive anesthetic drugs has been formulated as gels, so as to enable the drugs to exert their anesthetic effect before being washed off by saliva or removed by the tongue or inner lip. However, without the use of a cotton swab soaked in the gel and pressed against the tissue to be anesthetized for several minutes, non-satisfactory results are achieved.

In other cases, such as in cases of periodontal or endodontal abscess it is desirous to locally apply to an affected gingiva medicaments, such as antiseptic drugs, therapeutic drugs. In some cases it is desired to apply fluoride. No convenient means of locally applying such medicaments presently exists.

There is thus a widely recognized need for, and it would be highly advantageous to have, a device and method for local application of a medicament to a gingiva.

SUMMARY OF THE INVENTION

According to one aspect of the present invention there is provided a device for local application of a medicament to a gingiva, the device comprising (a) at least one absorbent body for absorbing the medicament; and (b) a biasing structure engaging the at least one absorbent body and being sized and so constructed so as to serve as a clip engagable over a tooth or several adjacent teeth of a maxilla or mandibula for biasing the at least one absorbent body against a portion of a maxillary gingiva or a mandibulary gingiva, respectively.

According to another aspect of the present invention there is provided a method of local application of a medicament to a gingiva, the method comprising the steps of (a) providing a device including (i) at least one absorbent body for absorbing the medicament; and (ii) a biasing structure engaging the at least one absorbent body and being sized and so constructed so as to serve as a clip engagable over a tooth or several adjacent teeth of a maxilla or mandibula for biasing the at least one absorbent body against a portion of a maxillary gingiva or a mandibulary gingiva, respectively; (b) loading a medicament on the at least one absorbent body; and (c) positioning the device over the teeth or several adjacent teeth of the maxilla or mandibula, thereby biasing the at least one absorbent body against the portion of the maxillary gingiva or the mandibulary gingiva, respectively.

According to yet another aspect of the present invention there is provided a method of local application of a medicament to a gingiva, the method comprising the steps of (a) providing a device including (i) at least one absorbent body for absorbing the medicament, the at least one absorbent body is loaded with the medicament; and (ii) a biasing structure engaging the at least one absorbent body and being sized and so constructed so as to serve as a clip engagable over a tooth or several adjacent teeth of a maxilla or mandibula for biasing the at least one absorbent body against a portion of a maxillary gingiva or a mandibulary gingiva, respectively; and (b) positioning the device over the teeth or several adjacent teeth of the maxilla or mandibula, thereby biasing the at least one absorbent body against the portion of the maxillary gingiva or the mandibulary gingiva, respectively.

According to further features in preferred embodiments of the invention described below, the device comprising two absorbent bodies for absorbing the medicament, each of the two absorbent bodies is engaged at an end of the biasing structure, such that when the biasing structure is positioned over the teeth or several adjacent teeth of the maxilla or the mandibula, the two absorbent bodies are biased against an inner and a corresponding outer portion of the maxillary gingiva or the mandibulary gingiva, respectively.

According to still further features in the described preferred embodiments each of the absorbent bodies is engaged with the biasing structure via a platform connected to, or integrally formed with an end of the biasing structure.

According to still further features in the described preferred embodiments the biasing structure is substantially U shaped.

According to still further features in the described preferred embodiments the biasing structure is made of a plastic material.

According to still further features in the described preferred embodiments each of the platforms is shaped so as to follow a contour of a portion of a gingiva.

According to still further features in the described preferred embodiments the device further comprising a whistling device, which is activated when the biasing structure is deformed or reformed.

According to still further features in the described preferred embodiments each of the platforms or absorbent bodies is shaped as a known figure.

According to still further features in the described preferred embodiments each of the absorbent bodies is preloaded with the medicament.

According to still further features in the described preferred embodiments the medicament is selected from the group consisting of a diffusive anesthetic drug, an antiseptic drug and a therapeutic drug.

According to still further features in the described preferred embodiments the diffusive anesthetic drug is selected from the group consisting of lignocaine and benzocaine, the antiseptic drug is selected from the group consisting of chlorhexidine, hydrogen peroxide and alcohol and the therapeutic drug is selected from the group consisting of antibiotics, corticosteroids and a fluor containing compound.

The present invention successfully addresses the shortcomings of the presently known configurations by providing a device and method for local application of a medicament to a gingiva before, during or after a dental treatment.

BRIEF DESCRIPTION OF THE DRAWINGS

The invention herein described, by way of example only, with reference to the accompanying drawings, wherein.

DESCRIPTION OF THE PREFERRED EMBODIMENTS

Figure 1:
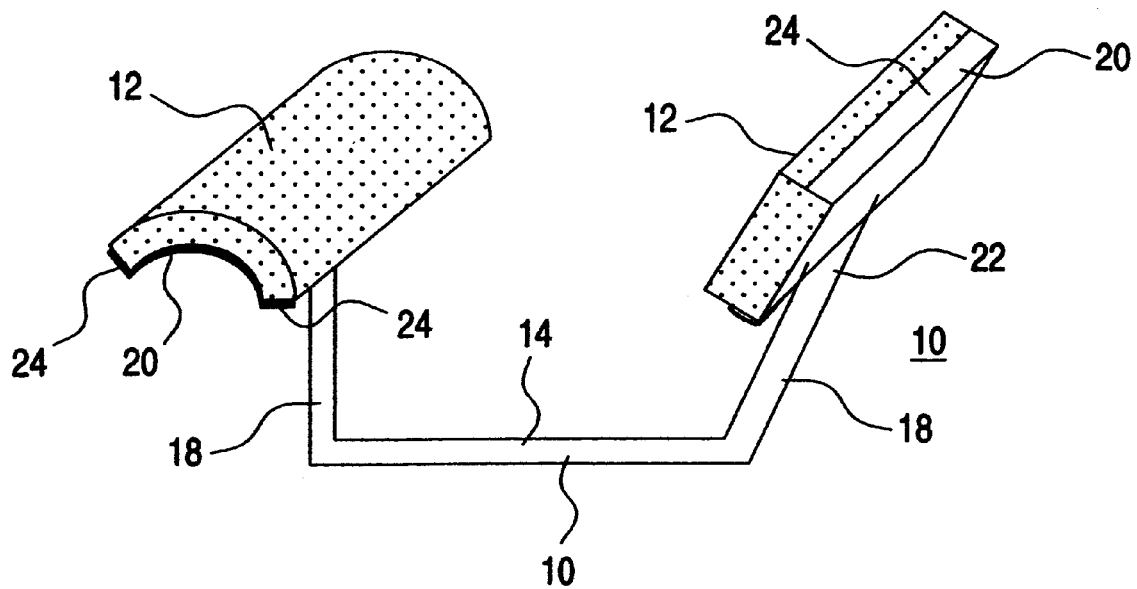
FIG. 1 is a perspective view of a device for local application of a medicament to a gingiva according to the present invention.

The present invention is of a device and method which can be used for local application of a medicament, such as, but not limited to, a local diffusive anesthetic drug, an antiseptic drug, and/or a therapeutic drug to a gingiva before, during or after a dental treatment. Specifically, the present invention can be used to apply local diffusive anesthetic prior to an intra gingival injection.

The principles and operation of the device and method for local application of a medicament to a gingiva according to the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Figure 2:
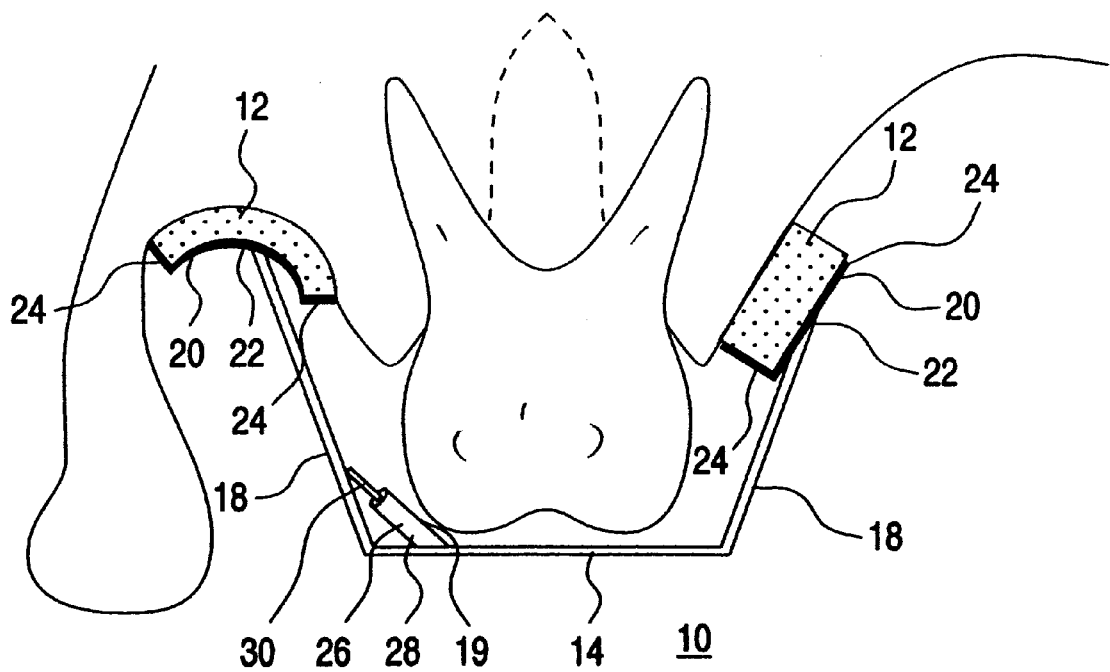
FIG. 2 is a cross-sectional view of the device for local application of a medicament to a gingiva according to the present invention when engaged over a tooth of a maxilla.

Referring now to the drawings, FIGS. 1–2 illustrate some preferred embodiments of the device for local application of a medicament to a gingiva according to the present invention, which device is referred to hereinbelow as device 10.

Device 10 includes at least one, preferably two, absorbent bodies 12. Bodies 12 serve for absorbing the medicament. The medicament can be applied to body or bodies 12 just prior to treatment. In this case, the active surface of body or bodies 12 is preferably formed with grooves for accepting the medicament. Alternatively, the medicament is preloaded onto body or bodies 12. Body 12 can be of any suitable absorbent, including, but not limited to, cotton, sponge either natural or synthetic, and the like. The type of material selected for body 12 depends on the formulation (liquid, gel, powder, etc.) of the medicament employed.

Device 10 further includes a biasing structure 14. Structure 14 engages body or bodies 12 and is sized and so constructed so as to serve as a clip engagable over a tooth or several adjacent teeth of a maxilla or mandibula, for biasing body or bodies 12 against a portion of a maxillary gingiva or a mandibulary gingiva, respectively.

The dimensions of each of body or bodies 12 can range from 25 to 100 mm$^2$ for a single tooth application or from 50 to 200 mm$^2$ for two teeth applications. Other dimensions are also envisaged. The shape of each of bodies 12 cab be, for example, but not limited to, round, elliptic, square, rectangle, triangle, polygonal, star, etc.

Biasing structure 14 is preferably substantially U shaped and therefore having a base element 16 and two arms 18 connected thereto or preferably integrally formed therewith. The length of base element 16 and of each of arms 18 is preferably about 0.8–1.2 cm. Arms 18 need not be parallel to one another nor they need to be vertical to base 16. Biasing structure 14 is preferably made of a plastic material. One ordinarily skilled in the art would know how to select a plastic material which will perform the above described biasing function, so as to allow efficient, convenient and useful functionality of device 10.

According to a preferred embodiment of the present invention each of absorbent bodies 12 is engaged with biasing structure 14 via a platform 20 connected to, or integrally formed with an end 22 of biasing structure 14. Each of platforms 20 preferably includes bent edges 24, so as to retain its corresponding body 12. Bodies 12 can be attached to platforms 20 using any adhesive which is inert (non-poisonous) and which withstands humidity. One ordinarily skilled in the art would know how to select a suitable adhesive. Specific platforms 20 can each be shaped so as to follow a contour of a portion of a gingiva. In the example of FIGS. 1–2, one of platforms 20 is curved so as to fit the contour of the maxillary buccal gingiva, whereas the other platform 20 is planar, so as to fit the planar contour of the maxillary palatinal gingiva. Alternatively, each of platforms 20 is made of a thin and flexible layer and is hingedly connected via an internal hinge at its respective end 22, so as to acquire the contour of the gingiva.

According to a preferred embodiment of the present invention bodies 12 and/or platforms 20 are shaped as a known figure, e.g., Donald duck, so as to render device 10 children friendly. Alternatively an application of a known figure is applied onto body or bodies 12.

According to a presently preferred embodiment of the present invention, and as specifically shown in FIG. 2, device 10 further includes a whistling device 26. Device 26 is activated when biasing structure 14 is deformed or reformed. Whistling device 26 is intended to encourage children under treatment to play with device 10 while in loco, so as to facilitate the diffusive transfer of the medicament therein to the treated gingiva. Device 26 can include a cylinder 28 connected at an end thereof to base element 16 and formed with a whistling aperture 29, and a translating rod 30 which is connected at an end thereof to one of arms 18 and translating in-and-out of cylinder 28 to thereby push of pull air through aperture 29, which, as a result, produces a whistling sound. Alternatively, device 26 can be implemented between one of platform 20 and its respective arm 18.

Any medicament in a liquid, gel or a dissolvable powder formulation can be preloaded or loaded on body or bodies 12.

Medicaments according to the present invention which are advantageously locally applied aided by device 10 can include any combination of a diffusive anesthetic drug, an antiseptic drug and a therapeutic drug.

The diffusive anesthetic drug can be, for example, but not limited to, lignocaine or benzocaine is a liquid or gel form. The antiseptic drug can be, for example, but not limited to, chlorhexidine, hydrogen peroxide or alcohol. The therapeutic drug can be, for example, but not limited to, an antibiotic (such as tetracycline) a corticosteroid and/or a fluor containing compound, in a liquid, gel or powder form.

Device 10 is preferably disposable and is provided wrapped and sterile.

According to another aspect of the present invention there is provided a method of local application of a medicament to a gingiva. the method according to this aspect of the invention is effected by implementing the following method steps, in which, in a first step, a device is provided including (i) at least one absorbent body for absorbing the medicament; and (ii) a biasing structure engaging the at least one absorbent body and being sized and so constructed so as to serve as a clip engagable over a tooth or several adjacent teeth of a maxilla or mandibula for biasing the at least one absorbent body against a portion of a maxillary gingiva or a mandibulary gingiva, respectively. In a second step of the method according to this aspect of the present invention a medicament is loaded on the at least one absorbent body. Finally, the device is positioned over the teeth or several adjacent teeth of the maxilla or mandibula, thereby biasing the at least one absorbent body against the portion of the maxillary gingiva or the mandibulary gingiva, respectively.

According to yet another aspect of the present invention there is provided a method of local application of a medicament to a gingiva. The method according to this aspect of the present invention is effected by implementing the following method steps, in which, in a first step, a device is provided including (i) at least one absorbent body for absorbing the medicament, the at least one absorbent body is loaded with the medicament; and (ii) a biasing structure engaging the at least one absorbent body and being sized and so constructed so as to serve as a clip engagable over a tooth or several adjacent teeth of a maxilla or mandibula for biasing the at least one absorbent body against a portion of a maxillary gingiva or a mandibulary gingiva, respectively. Then, the device is positioned over the teeth or several adjacent teeth of the maxilla or mandibula, thereby biasing the at least one absorbent body against the portion of the maxillary gingiva or the mandibulary gingiva, respectively.

By providing a device and method for local application of a medicament, such as, but not limited to, a local diffusive anesthetic drug, an antiseptic drug, and/or a therapeutic drug to a gingiva before, during or after a dental treatment the present invention improves the prior art practice, according to which, a cotton swab was employed for such applications.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

What is claimed is:

1. A device for local application of a medicament to a gingiva, the device comprising:
    (a) at least one absorbent body for absorbing the medicament; and
    (b) a biasing structure engaging said at least one absorbent body and being sized and so constructed so as to serve as a clip engagable over a tooth or several adjacent teeth of a maxilla or mandibula for biasing said at least one absorbent body against a portion of a maxillary gingiva or a mandibulary gingiva, respectively.

2. The device of claim 1, comprising two absorbent bodies for absorbing the medicament, each of said two absorbent bodies is engaged at an end of said biasing structure, such that when said biasing structure is positioned over said teeth or several adjacent teeth of said maxilla or said mandibula, said two absorbent bodies are biased against an inner and a corresponding outer portion of said maxillary gingiva or said mandibulary gingiva, respectively.

3. The device of claim 2, wherein each of said absorbent bodies is engaged with said biasing structure via a platform connected to, or integrally formed with an end of said biasing structure.

4. The device of claim 2, wherein said biasing structure is substantially U shaped.

5. The device of claim 2, wherein said biasing structure is made of a plastic material.

6. The device of claim 3, wherein each of said platforms is shaped so as to follow a contour of a portion of a gingiva.

7. The device of claim 2, further comprising a whistling device, which is activated when said biasing structure is deformed or reformed.

8. The device of claim 3, wherein each of said platforms or absorbent bodies is shaped as a known figure.

9. The device of claim 2, wherein each of said absorbent bodies is preloaded with the medicament.

10. The device of claim 9, wherein the medicament is selected from the group consisting of a diffusive anesthetic drug, an antiseptic drug and a therapeutic drug.

11. The device of claim 10, wherein said diffusive anesthetic drug is selected from the group consisting of lignocaine and benzocaine, said antiseptic drug is selected from the group consisting of chlorhexidine, hydrogen peroxide and alcohol and said therapeutic drug is selected from the group consisting of antibiotics, corticosteroids and a fluor containing compound.

12. A method of local application of a medicament to a gingiva, the method comprising the steps of:
    (a) providing a device including:
        (i) at least one absorbent body for absorbing the medicament; and
        (ii) a biasing structure engaging said at least one absorbent body and being sized and so constructed so as to serve as a clip engagable over a tooth or several adjacent teeth of a maxilla or mandibula for biasing said at least one absorbent body against a portion of a maxillary gingiva or a mandibulary gingiva, respectively;
    (b) loading a medicament on said at least one absorbent body; and
    (c) positioning said device over said teeth or several adjacent teeth of said maxilla or mandibula, thereby biasing said at least one absorbent body against said portion of said maxillary gingiva or said mandibulary gingiva, respectively.

13. The method of claim 12, wherein the medicament is selected from the group consisting of a diffusive anesthetic drug, an antiseptic drug and a therapeutic drug.

14. The method of claim 13, wherein said diffusive anesthetic drug is selected from the group consisting of lignocaine and benzocaine, said antiseptic drug is selected from the group consisting of chlorhexidine, hydrogen peroxide and alcohol and said therapeutic drug is selected from the group consisting of antibiotics, corticosteroids and a fluor containing compound.

15. A method of local application of a medicament to a gingiva, the method comprising the steps of:
  (a) providing a device including:
    (i) at least one absorbent body for absorbing the medicament, said at least one absorbent body is loaded with the medicament; and
    (ii) a biasing structure engaging said at least one absorbent body and being sized and so constructed so as to serve as a clip engagable over a tooth or several adjacent teeth of a maxilla or mandibula for biasing said at least one absorbent body against a portion of a maxillary gingiva or a mandibulary gingiva, respectively; and
  (b) positioning said device over said teeth or several adjacent teeth of said maxilla or mandibula, thereby biasing said at least one absorbent body against said portion of said maxillary gingiva or said mandibulary gingiva, respectively.

16. The method of claim 15, wherein the medicament is selected from the group consisting of a diffusive anesthetic drug, an antiseptic drug and a therapeutic drug.

17. The method of claim 16, wherein said diffusive anesthetic drug is selected from the group consisting of lignocaine and benzocaine, said antiseptic drug is selected from the group consisting of chlorhexidine, hydrogen peroxide and alcohol and said therapeutic drug is selected from the group consisting of antibiotics, corticosteroids and a fluor containing compound.

\* \* \* \* \*